United States Patent
Smirnov et al.

(10) Patent No.: US 11,253,360 B2
(45) Date of Patent: Feb. 22, 2022

(54) LOW PROFILE TISSUE ANCHOR FOR MINIMALLY INVASIVE HEART VALVE REPAIR

(71) Applicant: NeoChord, Inc., St. Louis Park, MN (US)

(72) Inventors: Alexei Smirnov, Boulder, CO (US); Graham Garvin, Redwood City, CA (US); Tim Crowley, Arvada, CO (US); Tom Broome, Mound, MN (US); Daryl Edmiston, Draper, UT (US)

(73) Assignee: NeoChord, Inc., St. Louis Park, MN (US)

( * ) Notice: Subject to any disclaimer, the term of this patent is extended or adjusted under 35 U.S.C. 154(b) by 0 days.

(21) Appl. No.: 16/406,736

(22) Filed: May 8, 2019

(65) Prior Publication Data

US 2019/0343626 A1    Nov. 14, 2019

Related U.S. Application Data

(60) Provisional application No. 62/669,096, filed on May 9, 2018.

(51) Int. Cl.
*A61B 17/04* (2006.01)
*A61F 2/24* (2006.01)
*A61B 17/00* (2006.01)

(52) U.S. Cl.
CPC ........ *A61F 2/2427* (2013.01); *A61B 17/0469* (2013.01); *A61F 2/2445* (2013.01);
(Continued)

(58) Field of Classification Search
CPC ............ A61B 17/0401; A61B 17/0469; A61B 2017/00243; A61F 2/2454; A61F 2/2457;
(Continued)

(56) References Cited

U.S. PATENT DOCUMENTS

| 2,751,908 A | 6/1956 | Wallace |
| 3,664,330 A | 5/1972 | Deutsch |

(Continued)

FOREIGN PATENT DOCUMENTS

| EP | 1039851 B1 | 7/2005 |
| EP | 1637091 A2 | 3/2006 |

(Continued)

OTHER PUBLICATIONS

Interactive Cardio Vascular and Thoracic Surgery; Abstracts; Suppl 3 to vol. 7 (Sep. 2008) 52 pages.
(Continued)

*Primary Examiner* — Dinah Baria
(74) *Attorney, Agent, or Firm* — Patterson Thuente Pedersen, P.A.

(57) ABSTRACT

Various embodiments of anchors are configured to be inserted into a heart wall of a patient to anchor a suture as an artificial chordae under an appropriate tension for proper valve function. Each of the disclosed anchor embodiments "toggles" from a first position for delivery of the anchor to the heart wall and a second position for insertion of the anchor into the heart wall. In some embodiments, it is the "toggle" to the second position that provides the insertion force for inserting the anchor into the heart muscle sufficient to retain the anchor from accidental withdrawal from the heart wall during normal valve operation (e.g., when a valve leaflet pulls on the suture attached to the anchor during systole). Such anchors are particularly suitable for use in intravascular, transcatheter procedures as described above given the inherent difficulties in providing sufficient force for insertion of an anchor into the heart wall with a flexible catheter.

16 Claims, 16 Drawing Sheets

(52) U.S. Cl.
CPC . *A61B 17/0401* (2013.01); *A61B 2017/00243* (2013.01); *A61F 2/2457* (2013.01)

(58) Field of Classification Search
CPC ............ A61F 2220/0016; A61F 2/2427; A61F 2/2445
See application file for complete search history.

(56) References Cited

U.S. PATENT DOCUMENTS

| | | | |
|---|---|---|---|
| 3,667,474 A | 6/1972 | Lapkin | |
| 3,842,840 A | 10/1974 | Schweizer | |
| 4,258,716 A | 3/1981 | Sutherland | |
| 4,351,345 A | 9/1982 | Carney | |
| 4,759,348 A | 7/1988 | Cawood | |
| 4,836,204 A | 6/1989 | Landymore et al. | |
| 4,935,027 A | 6/1990 | Yoon | |
| 4,957,498 A | 9/1990 | Caspari et al. | |
| 4,967,498 A | 9/1990 | Caspari | |
| 4,960,424 A | 10/1990 | Grooters | |
| 4,967,798 A | 11/1990 | Hammer | |
| 4,972,874 A | 11/1990 | Jackson | |
| 5,053,013 A | 10/1991 | Ensminger | |
| 5,059,201 A | 10/1991 | Asnis | |
| 5,211,650 A | 5/1993 | Noda | |
| 5,297,536 A | 3/1994 | Wilk | |
| 5,304,185 A | 4/1994 | Taylor | |
| 5,312,423 A | 5/1994 | Rosenbluth et al. | |
| 5,336,229 A | 8/1994 | Noda | |
| 5,383,877 A | 1/1995 | Clarke | |
| 5,431,666 A | 7/1995 | Sauer et al. | |
| 5,452,733 A | 9/1995 | Sterman | |
| 5,474,519 A | 12/1995 | Bloomer | |
| 5,547,455 A | 8/1996 | McKenna et al. | |
| 5,556,411 A | 9/1996 | Taoda et al. | |
| 5,571,215 A | 11/1996 | Sterman | |
| 5,601,578 A | 2/1997 | Murphy | |
| 5,626,607 A | 5/1997 | Malecki | |
| 5,653,716 A | 8/1997 | Malo et al. | |
| 5,662,704 A | 9/1997 | Gross | |
| 5,665,100 A | 9/1997 | Yoon | |
| 5,667,472 A | 9/1997 | Finn et al. | |
| 5,667,473 A | 9/1997 | Finn et al. | |
| 5,667,478 A | 9/1997 | McFarlin et al. | |
| 5,693,091 A | 12/1997 | Larson, Jr. et al. | |
| 5,728,113 A | 3/1998 | Sherts | |
| 5,762,458 A | 6/1998 | Wang et al. | |
| 5,762,613 A | 6/1998 | Sutton et al. | |
| 5,766,163 A | 6/1998 | Mueller et al. | |
| 5,769,791 A | 6/1998 | Benaron et al. | |
| 5,772,597 A | 6/1998 | Goldberger et al. | |
| 5,772,672 A | 6/1998 | Toy et al. | |
| 5,785,658 A | 7/1998 | Benaron et al. | |
| 5,797,960 A | 8/1998 | Stevens et al. | |
| 5,830,231 A | 11/1998 | Geiges, Jr. | |
| 5,839,639 A | 11/1998 | Sauer et al. | |
| 5,857,961 A | 1/1999 | Vanden Hoek et al. | |
| 5,897,564 A | 4/1999 | Schulze et al. | |
| 5,908,428 A | 6/1999 | Scirica et al. | |
| 5,908,429 A | 6/1999 | Yoon | |
| 5,919,128 A | 7/1999 | Fitch | |
| 5,961,440 A | 10/1999 | Schweich, Jr. | |
| 5,972,004 A | 10/1999 | Williamson et al. | |
| 5,972,030 A | 10/1999 | Garrison et al. | |
| 5,984,939 A | 11/1999 | Yoon | |
| 5,993,466 A | 11/1999 | Yoon | |
| 5,993,467 A | 11/1999 | Yoon | |
| 6,022,360 A | 2/2000 | Reimels et al. | |
| 6,045,497 A | 4/2000 | Schweich, Jr. | |
| 6,050,936 A | 4/2000 | Schweich, Jr. | |
| 6,053,933 A | 4/2000 | Balazs et al. | |
| 6,059,715 A | 5/2000 | Schweich, Jr. | |
| 6,074,417 A | 6/2000 | Peredo | |
| 6,077,214 A | 6/2000 | Mortier et al. | |
| 6,117,144 A | 9/2000 | Nobles et al. | |
| 6,129,683 A | 10/2000 | Sutton et al. | |
| 6,149,660 A | 11/2000 | Laufer et al. | |
| 6,152,934 A | 11/2000 | Harper et al. | |
| 6,162,168 A | 12/2000 | Schweich, Jr. | |
| 6,162,233 A | 12/2000 | Williamson | |
| 6,165,119 A | 12/2000 | Schweich, Jr. | |
| 6,165,120 A | 12/2000 | Schweich, Jr. | |
| 6,165,183 A | 12/2000 | Kuehn et al. | |
| 6,178,346 B1 | 1/2001 | Amundson et al. | |
| 6,179,195 B1 | 1/2001 | Adams et al. | |
| 6,183,411 B1 | 2/2001 | Mortier et al. | |
| 6,190,357 B1 | 2/2001 | Ferrari et al. | |
| 6,234,079 B1 | 5/2001 | Chertkow | |
| 6,234,995 B1 | 5/2001 | Peacock, III | |
| 6,245,079 B1 | 6/2001 | Nobles et al. | |
| 6,260,552 B1 | 7/2001 | Mortier et al. | |
| 6,261,222 B1 | 7/2001 | Schweich, Jr. | |
| 6,264,602 B1 | 7/2001 | Mortier et al. | |
| 6,269,819 B1 | 8/2001 | Oz et al. | |
| 6,270,508 B1 | 8/2001 | KlIeman et al. | |
| 6,283,993 B1 | 9/2001 | Cosgrove et al. | |
| 6,312,447 B1 | 11/2001 | Grimes | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,355,050 B1 | 3/2002 | Andreas et al. | |
| 6,401,720 B1 | 6/2002 | Stevens et al. | |
| 6,402,679 B1 | 6/2002 | Mortier et al. | |
| 6,402,680 B2 | 6/2002 | Mortier et al. | |
| 6,402,781 B1 | 6/2002 | Langberg et al. | |
| 6,406,420 B1 | 6/2002 | McCarthy et al. | |
| 6,419,626 B1 | 7/2002 | Yoon | |
| 6,436,107 B1 | 8/2002 | Wang et al. | |
| 6,443,922 B1 | 9/2002 | Roberts et al. | |
| 6,451,054 B1 | 9/2002 | Stevens | |
| 6,461,366 B1 | 10/2002 | Seguin | |
| 6,508,777 B1 | 1/2003 | Macoviak et al. | |
| 6,514,194 B2 | 2/2003 | Schweich, Jr. et al. | |
| 6,533,796 B1 | 3/2003 | Sauer et al. | |
| 6,537,198 B1 | 3/2003 | Vidlund et al. | |
| 6,537,314 B2 | 3/2003 | Langberg et al. | |
| 6,551,331 B2 | 4/2003 | Nobles et al. | |
| 6,558,416 B2 | 5/2003 | Cosgrove et al. | |
| 6,562,052 B2 | 5/2003 | Nobles et al. | |
| 6,564,805 B2 | 5/2003 | Garrison et al. | |
| 6,582,388 B1 | 6/2003 | Coleman et al. | |
| 6,585,727 B1 | 7/2003 | Cashman et al. | |
| 6,589,160 B2 | 7/2003 | Schweich, Jr. et al. | |
| 6,602,288 B1 | 8/2003 | Cosgrove et al. | |
| 6,616,684 B1 | 9/2003 | Vidlund et al. | |
| 6,619,291 B2 | 9/2003 | Hlavka et al. | |
| 6,622,730 B2 | 9/2003 | Ekvall et al. | |
| 6,626,917 B1 | 9/2003 | Craig | |
| 6,626,930 B1 | 9/2003 | Allen et al. | |
| 6,629,534 B1 | 10/2003 | St. Goar et al. | |
| 6,629,921 B1 | 10/2003 | Schweich, Jr. et al. | |
| 6,629,984 B1 | 10/2003 | Chan | |
| 6,645,205 B2 | 11/2003 | Ginn | |
| 6,679,268 B2 | 1/2004 | Stevens et al. | |
| 6,692,605 B2 | 2/2004 | Kerr et al. | |
| 6,695,866 B1 | 2/2004 | Kuehn et al. | |
| 6,709,456 B2 | 3/2004 | Langberg et al. | |
| 6,718,985 B2 | 4/2004 | Hlavka et al. | |
| 6,723,038 B1 | 4/2004 | Schroeder et al. | |
| 6,733,509 B2 | 5/2004 | Nobles et al. | |
| 6,740,107 B2 | 5/2004 | Loeb et al. | |
| 6,743,239 B1 | 6/2004 | Kuehn et al. | |
| 6,746,471 B2 | 6/2004 | Mortier et al. | |
| 6,752,713 B2 | 6/2004 | Johnson, Jr. | |
| 6,752,813 B2 | 6/2004 | Goldfarb et al. | |
| 6,755,777 B2 | 6/2004 | Schweich, Jr. et al. | |
| 6,764,510 B2 | 7/2004 | Vidlund et al. | |
| 6,770,083 B2 | 8/2004 | Seguin | |
| 6,770,084 B1 | 8/2004 | Bain et al. | |
| 6,793,618 B2 | 9/2004 | Schweich, Jr. et al. | |
| 6,802,860 B2 | 10/2004 | Cosgrove et al. | |
| 6,808,488 B2 | 10/2004 | Mortier et al. | |
| 6,810,882 B2 | 11/2004 | Langberg et al. | |
| 6,840,246 B2 | 1/2005 | Downing | |
| 6,858,003 B2 | 2/2005 | Evans et al. | |

(56) References Cited

U.S. PATENT DOCUMENTS

| | | |
|---|---|---|
| 6,875,224 B2 | 4/2005 | Grimes |
| 6,893,448 B2 | 5/2005 | O'Quinn et al. |
| 6,896,686 B2 | 5/2005 | Weber |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,303,622 B2 | 11/2012 | Alkhatib |
| 8,465,500 B2 | 6/2013 | Speziali |
| 8,512,362 B2 | 8/2013 | Ewers et al. |
| 8,545,551 B2 | 10/2013 | Loulmet |
| 8,758,393 B2 | 6/2014 | Zentgraf |
| 8,771,296 B2 | 7/2014 | Nobles et al. |
| 8,938,283 B2 | 1/2015 | Zentgraf et al. |
| 8,968,338 B2 | 3/2015 | Speziali |
| 9,044,221 B2 | 6/2015 | Zentgraf et al. |
| 9,192,374 B2 | 11/2015 | Zentgraf |
| 9,364,213 B2 | 6/2016 | Speziali |
| 9,393,080 B2 | 7/2016 | Zentgraf et al. |
| 9,572,556 B2 | 2/2017 | Skinlo et al. |
| 9,668,860 B2 | 6/2017 | Kudlik et al. |
| 9,700,300 B2 | 7/2017 | Speziali |
| 9,877,833 B1 | 1/2018 | Bishop et al. |
| 10,080,659 B1 | 9/2018 | Zentgraf et al. |
| 10,130,474 B2 | 11/2018 | Zentgraf et al. |
| 10,213,306 B2 | 2/2019 | Colli |
| 10,314,586 B2 | 6/2019 | Greenberg et al. |
| 10,327,743 B2 | 6/2019 | St. Goar et al. |
| 10,499,941 B2 | 12/2019 | Suri |
| 10,507,018 B2 | 12/2019 | Zentgraf |
| 10,582,924 B2 | 3/2020 | Speziali |
| 10,588,620 B2 | 3/2020 | Caffes et al. |
| 10,695,178 B2 | 6/2020 | Zentgraf et al. |
| 10,765,715 B2 | 9/2020 | Kang et al. |
| 2001/0005787 A1 | 6/2001 | Oz |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0020732 A1 | 2/2002 | Adams et al. |
| 2002/0029080 A1 | 3/2002 | Mortier et al. |
| 2002/0049402 A1 | 4/2002 | Peacock, III |
| 2002/0077524 A1 | 6/2002 | Schweich, Jr. |
| 2002/0091382 A1 | 7/2002 | Hooven |
| 2002/0169359 A1 | 11/2002 | McCarthy |
| 2002/0173694 A1 | 11/2002 | Mortier et al. |
| 2002/0183766 A1 | 12/2002 | Seguin |
| 2002/0183787 A1 | 12/2002 | Wahr et al. |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano |
| 2003/0078599 A1 | 4/2003 | O'Quinn et al. |
| 2003/0078600 A1 | 4/2003 | O'Quinn et al. |
| 2003/0105519 A1 | 6/2003 | Fasol |
| 2003/0120341 A1 | 6/2003 | Shennib et al. |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr. |
| 2003/0167071 A1 | 9/2003 | Martin et al. |
| 2003/0171641 A1 | 9/2003 | Schweich, Jr. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0093023 A1 | 5/2004 | Allen et al. |
| 2004/0097805 A1 | 5/2004 | Verard et al. |
| 2004/0116767 A1 | 6/2004 | Lebovic |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0220593 A1 | 11/2004 | Grennhalgh |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0236373 A1 | 11/2004 | Anspach, III |
| 2004/0243229 A1 | 12/2004 | Vidlund et al. |
| 2004/0267083 A1 | 12/2004 | McCarthy |
| 2005/0004668 A1 | 1/2005 | Aklog et al. |
| 2005/0021055 A1 | 1/2005 | Toubia et al. |
| 2005/0021056 A1 | 1/2005 | St. Goar |
| 2005/0021057 A1 | 1/2005 | St. Goar |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich, Jr. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove |
| 2005/0216039 A1 | 9/2005 | Lederman |

(56) References Cited

U.S. PATENT DOCUMENTS

| | | |
|---|---|---|
| 2005/0240202 A1 | 10/2005 | Shennib et al. |
| 2005/0251187 A1 | 11/2005 | Beane et al. |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074484 A1 | 4/2006 | Huber |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0106305 A1* | 5/2006 | Lau .................. A61F 2/2451 600/431 |
| 2006/0127509 A1 | 6/2006 | Eckman |
| 2006/0135993 A1 | 6/2006 | Seguin |
| 2006/0149123 A1 | 7/2006 | Vidlund et al. |
| 2006/0161040 A1 | 7/2006 | McCarthy |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0241340 A1 | 10/2006 | Vidlund |
| 2006/0287657 A1 | 12/2006 | Bachman |
| 2007/0002627 A1 | 1/2007 | Youn |
| 2007/0027451 A1 | 2/2007 | Desinger et al. |
| 2007/0038293 A1 | 2/2007 | St. Goar et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0118151 A1 | 5/2007 | Davidson |
| 2007/0118154 A1 | 5/2007 | Crabtree |
| 2007/0118155 A1 | 5/2007 | Goldfarb et al. |
| 2007/0118213 A1 | 5/2007 | Loulmet |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0213582 A1 | 9/2007 | Zollinger et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton, Jr. et al. |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125860 A1 | 5/2008 | Webler |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195126 A1 | 8/2008 | Solem |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0243245 A1 | 10/2008 | Thamber et al. |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0125038 A1 | 5/2009 | Ewers et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. |
| 2009/0192598 A1 | 7/2009 | Lattouf et al. |
| 2009/0259304 A1 | 10/2009 | O'Beirne et al. |
| 2010/0030061 A1 | 2/2010 | Canfield et al. |
| 2010/0030242 A1 | 2/2010 | Nobles et al. |
| 2010/0042147 A1 | 2/2010 | Janovsky et al. |
| 2010/0121349 A1 | 5/2010 | Meier et al. |
| 2010/0160726 A1 | 6/2010 | Windheuser |
| 2010/0174297 A1 | 7/2010 | Speziali |
| 2010/0185172 A1 | 7/2010 | Fabro |
| 2010/0217283 A1 | 8/2010 | St. Goar |
| 2010/0298929 A1 | 11/2010 | Thornton et al. |
| 2011/0011917 A1 | 1/2011 | Loulmet |
| 2012/0184971 A1 | 7/2012 | Zentgraf et al. |
| 2013/0035757 A1 | 2/2013 | Zentgraf et al. |
| 2013/0150710 A1 | 6/2013 | Zentgraf et al. |
| 2013/0158600 A1 | 6/2013 | Conklin et al. |
| 2014/0031926 A1 | 1/2014 | Kudlik et al. |
| 2014/0039324 A1 | 2/2014 | Speziali |
| 2014/0364875 A1 | 12/2014 | Zentgraf |
| 2015/0148821 A1 | 5/2015 | Speziali |
| 2015/0190207 A1 | 7/2015 | Zentgraf et al. |
| 2015/0313620 A1 | 11/2015 | Suri |
| 2015/0313713 A1 | 11/2015 | Zentgraf et al. |
| 2015/0351741 A1 | 12/2015 | Hawkins |
| 2015/0351910 A1 | 12/2015 | Gilmore et al. |
| 2015/0366556 A1 | 12/2015 | Khairkhahan et al. |
| 2016/0106420 A1 | 4/2016 | Foerster et al. |
| 2016/0143737 A1 | 5/2016 | Zentgraf et al. |
| 2017/0245994 A1 | 8/2017 | Khairkhahan et al. |
| 2017/0290582 A1 | 10/2017 | Speziali |
| 2018/0161035 A1 | 6/2018 | Greenberg et al. |
| 2018/0185153 A1 | 7/2018 | Bishop et al. |
| 2018/0280138 A1 | 10/2018 | Colli |
| 2018/0289483 A1 | 10/2018 | Kang et al. |
| 2019/0053902 A1 | 2/2019 | Zentgraf et al. |
| 2019/0133766 A1 | 5/2019 | Zentgraf et al. |
| 2019/0216601 A1 | 7/2019 | Purcell et al. |
| 2019/0224012 A1 | 7/2019 | Colli |
| 2019/0290260 A1 | 9/2019 | Caffes et al. |
| 2019/0343633 A1 | 11/2019 | Garvin et al. |
| 2019/0343634 A1 | 11/2019 | Garvin et al. |
| 2020/0093478 A1 | 3/2020 | Caffes et al. |
| 2020/0121314 A1 | 4/2020 | Speziali |
| 2020/0138430 A1 | 5/2020 | Zentgraf |
| 2020/0222186 A1 | 7/2020 | Edmiston et al. |
| 2020/0281582 A1 | 9/2020 | Caffes et al. |
| 2020/0330228 A1 | 10/2020 | Anderson et al. |
| 2020/0368022 A1 | 11/2020 | Zentgraf et al. |

FOREIGN PATENT DOCUMENTS

| | | |
|---|---|---|
| EP | 1845861 A2 | 10/2007 |
| EP | 1408850 B1 | 9/2009 |
| EP | 3441045 A1 | 2/2019 |
| JP | H 04307052 A | 10/1992 |
| JP | 06142114 | 5/1994 |
| JP | 2004-531337 | 10/2004 |
| JP | 2007-535342 | 12/2007 |
| WO | WO 1999/00059 A1 | 1/1999 |
| WO | WO 1999/30647 A1 | 6/1999 |
| WO | WO 2000/06026 A2 | 2/2000 |
| WO | WO 2000/06027 A2 | 2/2000 |
| WO | WO 2000/06028 A1 | 2/2000 |
| WO | WO 2000/16700 A1 | 3/2000 |
| WO | WO 2001/66018 A1 | 9/2001 |
| WO | WO 2001/95809 A1 | 12/2001 |
| WO | WO 2003/001893 A2 | 1/2003 |
| WO | WO 2003/059209 A2 | 7/2003 |
| WO | WO 2003/079937 A2 | 10/2003 |
| WO | WO 2003/082157 A2 | 10/2003 |
| WO | WO 2003/082158 A1 | 10/2003 |
| WO | WO 2004/021893 A1 | 3/2004 |
| WO | WO 2004/043265 A2 | 5/2004 |
| WO | WO 2005/039428 A2 | 5/2005 |
| WO | WO 2005/087140 A1 | 9/2005 |
| WO | WO 2005/094525 A2 | 10/2005 |
| WO | WO 2006/012750 A1 | 2/2006 |
| WO | WO 2006/032051 A2 | 3/2006 |
| WO | WO 2006/065966 A2 | 6/2006 |
| WO | WO 2006/078694 A2 | 7/2006 |

(56) References Cited

FOREIGN PATENT DOCUMENTS

| | | |
|---|---|---|
| WO | WO 2006/116310 A2 | 11/2006 |
| WO | WO 2006/127509 A2 | 11/2006 |
| WO | WO 2007/002627 A1 | 1/2007 |
| WO | WO 2007/027451 A2 | 3/2007 |
| WO | WO 2007/062128 A2 | 5/2007 |
| WO | WO 2007/081418 A1 | 7/2007 |
| WO | WO 2007/117612 A1 | 10/2007 |
| WO | WO 2008/010738 A2 | 1/2008 |
| WO | WO 2009/052528 A2 | 4/2009 |
| WO | WO 2011/070477 A1 | 6/2011 |
| WO | WO 2011/137336 A1 | 11/2011 |
| WO | WO 2012/167120 A2 | 12/2012 |
| WO | WO 2018/236766 A1 | 12/2018 |
| WO | WO 2019/183626 A1 | 9/2019 |
| WO | WO 2019/217638 A1 | 1/2020 |

OTHER PUBLICATIONS

Machine translation of JP 06142114.

Port Access System for Mitral Valve Repair Proves Its Value in Study; MedGadget Jul. 9, 2009 (2 pages).

PCT/US2019/031451, Search Report and Written Opinion dated Sep. 17, 2019, 16 pages.

Application and File History for U.S. Appl. No. 13/486,632, filed Jun. 1, 2012. Inventor Zentgraf et al.

Application and File History for U.S. Appl. No. 14/947,399, filed Nov. 20, 2015. Inventors: Zentgraf et al.

Application and File History for U.S. Appl. No. 16/905,645, filed Jun. 18, 2020. Inventors: Zentgraf et al.

Application and File History for U.S. Appl. No. 16/406,764, filed May 8, 2019. Inventors: Garvin et al.

Application and File History for U.S. Appl. No. 16/406,799, filed May 8, 2019. Inventors: Garvin et al.

Application and File History for U.S. Appl. No. 16/818,639, filed Mar. 13, 2020. Inventors: Caffes et al.

Application and File History for U.S. Appl. No. 16/363,701, filed Mar. 25, 2019. Inventors: Caffes et al.

Application and File History for U.S. Appl. No. 16/850,827, filed Apr. 16, 2020. Inventors: Anderson et al.

Application and File History for U.S. Appl. No. 16/564,887, filed Sep. 9, 2019. Inventors: Caffes et al.

* cited by examiner

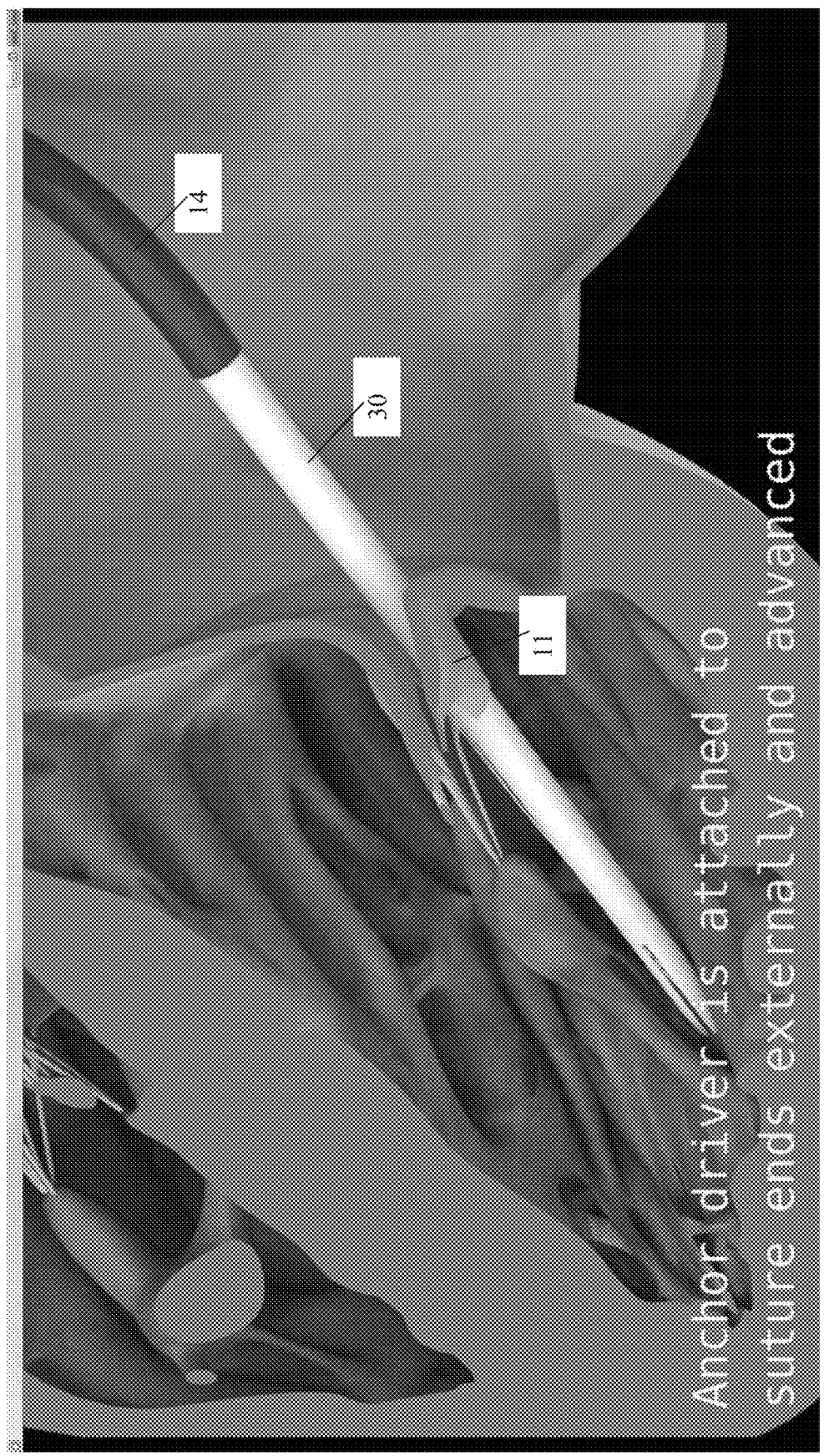
Fig. 1C Anchor driver is attached to suture ends externally and advanced

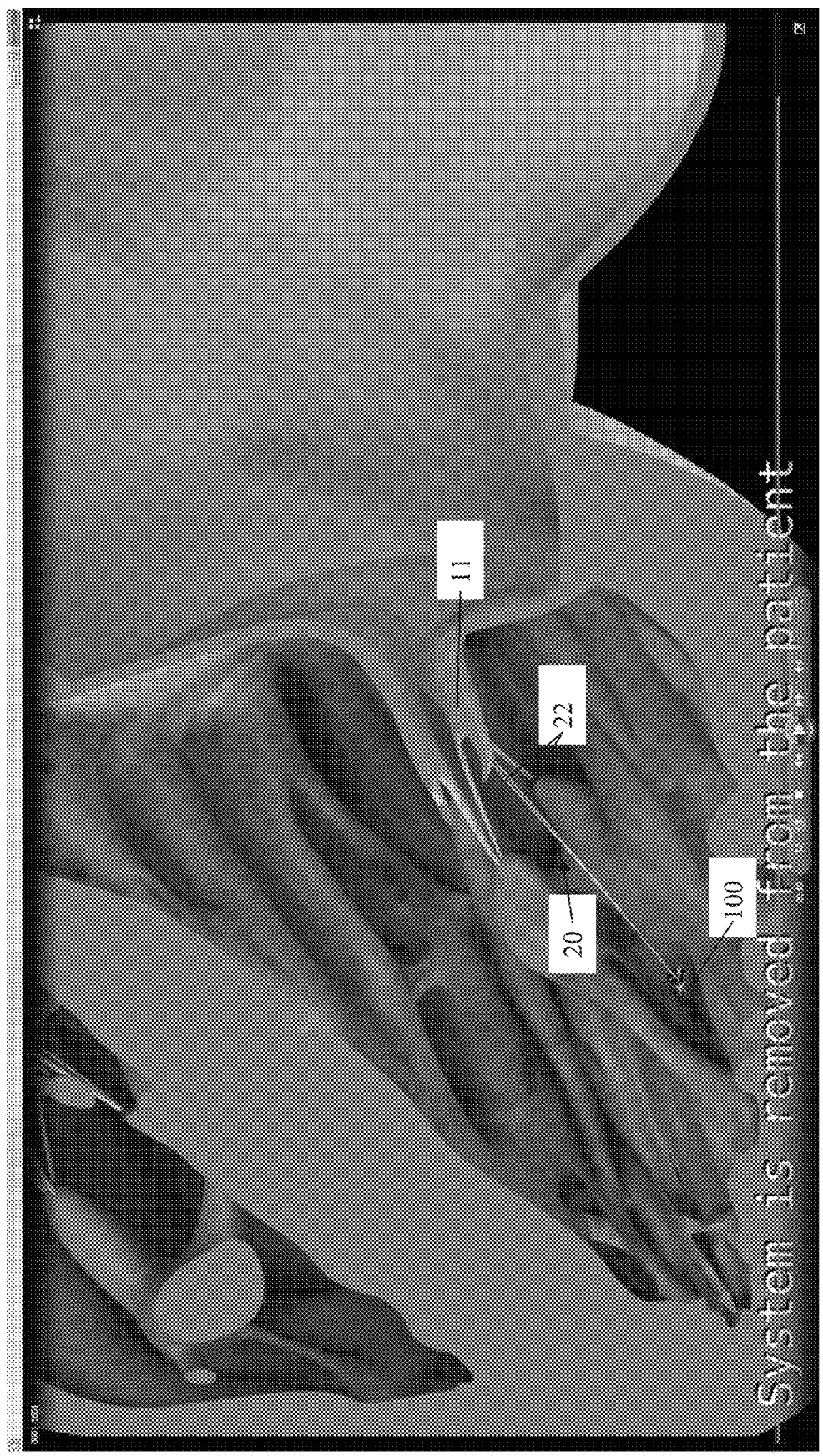

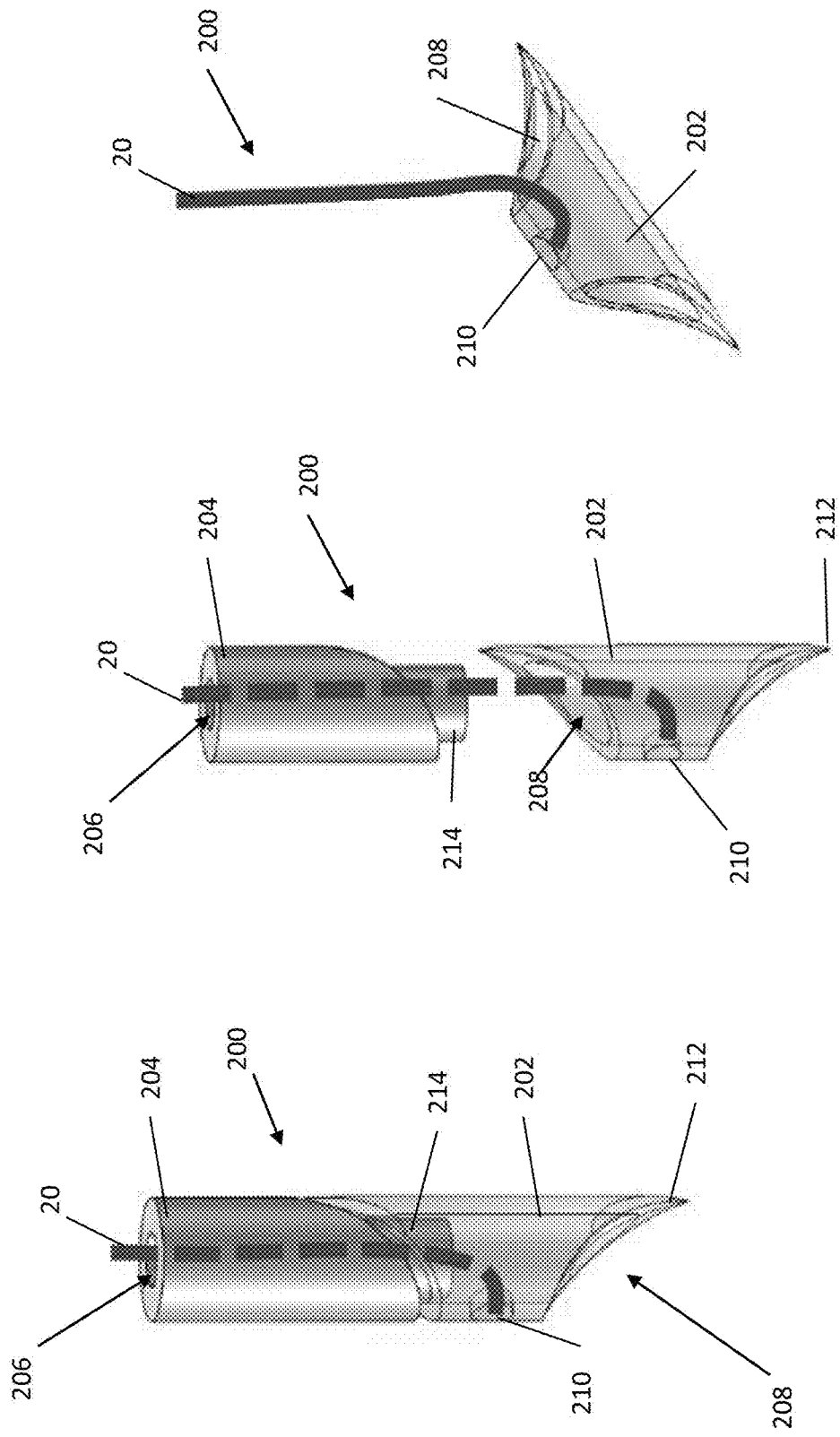

LOW PROFILE TISSUE ANCHOR FOR MINIMALLY INVASIVE HEART VALVE REPAIR

RELATED APPLICATION

This application claims the benefit of U.S. Provisional Application No. 62/669,096 filed May 9, 2018, which is hereby fully incorporated herein by reference.

TECHNICAL FIELD

The present invention relates to minimally invasive delivery of a suture. More particularly, the present invention relates to anchoring of a suture as an artificial chordae tendineae for a flailing or prolapsing leaflet in a beating heart.

BACKGROUND

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle.

This technique for implantation of artificial chordae was traditionally done by an open heart operation generally carried out through a median sternotomy and requiring cardiopulmonary bypass with aortic cross-clamp and cardioplegic arrest of the heart. Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of an artificial chordae through the atriotomy for attachment within the heart. However, these invasive open heart procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of such techniques.

Techniques for minimally invasive thoracoscopic repair of heart valves while the heart is still beating have also been developed. U.S. Pat. No. 8,465,500 to Speziali, which is incorporated by reference herein, discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. More recent versions of these techniques are disclosed in U.S. Pat. Nos. 8,758,393 and 9,192,374 to Zentgraf, which disclose an integrated device that can enter the heart chamber, navigate to the leaflet, capture the leaflet, confirm proper capture, and deliver a suture as part of a mitral valve regurgitation (MR) repair. These minimally invasive repairs are generally performed through a small, between the ribs access point followed by a puncture into the ventricle through the apex of the heart. Although far less invasive and risky for the patient than an open heart procedure, these procedures still require significant recovery time and pain.

Some systems have therefore been proposed that utilize a catheter routed through the patient's vasculature to enter the heart and attach a suture to a heart valve leaflet as an artificial chordae. While generally less invasive than the approaches discussed above, transcatheter heart valve repair can provide additional challenges. For example, with all artificial chordae replacement procedures, in addition to inserting a suture through a leaflet, the suture must also be anchored at a second location, such as at a papillary muscle in the heart, with a suture length, tension and positioning of the suture that enables the valve to function naturally. If the suture is too short and/or has too much tension, the valve leaflets may not properly close. Conversely, if the suture is too long and/or does not have enough tension, the valve leaflets may still be subject to prolapse. Proper and secure anchoring of the suture away from the leaflet is therefore a critical aspect of any heart valve repair procedure for inserting an artificial chordae. In the case of transcatheter procedures, such anchoring can be difficult because it can be difficult for the flexible catheter required for routing through the patient's vasculature to apply sufficient force to stably insert traditional suture anchors into, e.g., the myocardium.

SUMMARY

Disclosed herein are various embodiments of anchors configured to be inserted into a heart wall of a patient to anchor a suture as an artificial chordae under an appropriate tension for proper valve function. Each of the disclosed anchor embodiments "toggles" from a first position for delivery of the anchor to the heart wall and a second position for insertion of the anchor into the heart wall. In some embodiments, it is the "toggle" to the second position that provides the necessary insertion force for inserting the anchor into the heart muscle sufficient to retain the anchor from accidental withdrawal from the heart wall during normal valve operation (e.g., when a valve leaflet pulls on the suture attached to the anchor during systole). Such anchors are particularly suitable for use in intravascular, transcatheter procedures as described above given the inherent difficulties in providing sufficient force for insertion of an anchor into the heart wall with a flexible catheter.

In one embodiment, a method of anchoring a suture in a patient's heart as an artificial chordae includes intravascularly accessing a patient's heart and inserting a suture into a heart valve leaflet of the patient's heart. A portion of the suture can be attached to a low profile tissue anchor or "toggle anchor" including an anchor body and an anchor tip. The toggle anchor can be inserted into the patient's heart intravascularly with an anchor delivery catheter with the toggle anchor in a delivery position having the anchor tip extending generally axially with respect to the anchor body such that the toggle anchor fits within the anchor delivery catheter and is configured to be positioned adjacent a heart wall of the patient's heart. The toggle anchor can then be advanced out of the anchor delivery catheter and into the heart wall such that the toggle anchor transitions from the delivery position into an anchoring position with the anchor tip being oriented generally transverse to the anchor body as the toggle anchor is advanced into the heart wall in the anchoring position. In some embodiments, the transition from the delivery position to the anchoring position provides a force sufficient to cause the anchor tip to penetrate into the heart wall. The anchor delivery catheter can then be removed from the heart leaving the toggle anchor in the heart with the suture extending between the leaflet and the toggle anchor as an artificial chordae.

In one embodiment, an anchor is configured to be implanted into a patient's heart wall to anchor a suture extending from a valve leaflet of the heart as an artificial chordae. The anchor can include an anchor shaft and an anchor tip extending from a distal end of the anchor shaft. The anchor tip can be configured for delivery to the heart wall in a delivery configuration generally axially aligned with the anchor shaft such that the anchor shaft and anchor tip can be contained within an anchor delivery catheter. The anchor tip can further be configured to toggle from the delivery configuration into an anchor configuration when advanced out of the anchor delivery catheter and into the heart wall with the anchor tip being generally transverse to the anchor shaft in the anchor configuration to retain the anchor within the heart wall.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1K depict various steps in a method of anchoring a suture in a beating heart of a patient to function as an artificial chordae according to an embodiment.

FIGS. 4A-4C depict a low profile tissue anchor for an artificial chordae according to an embodiment.

Figure 1A:
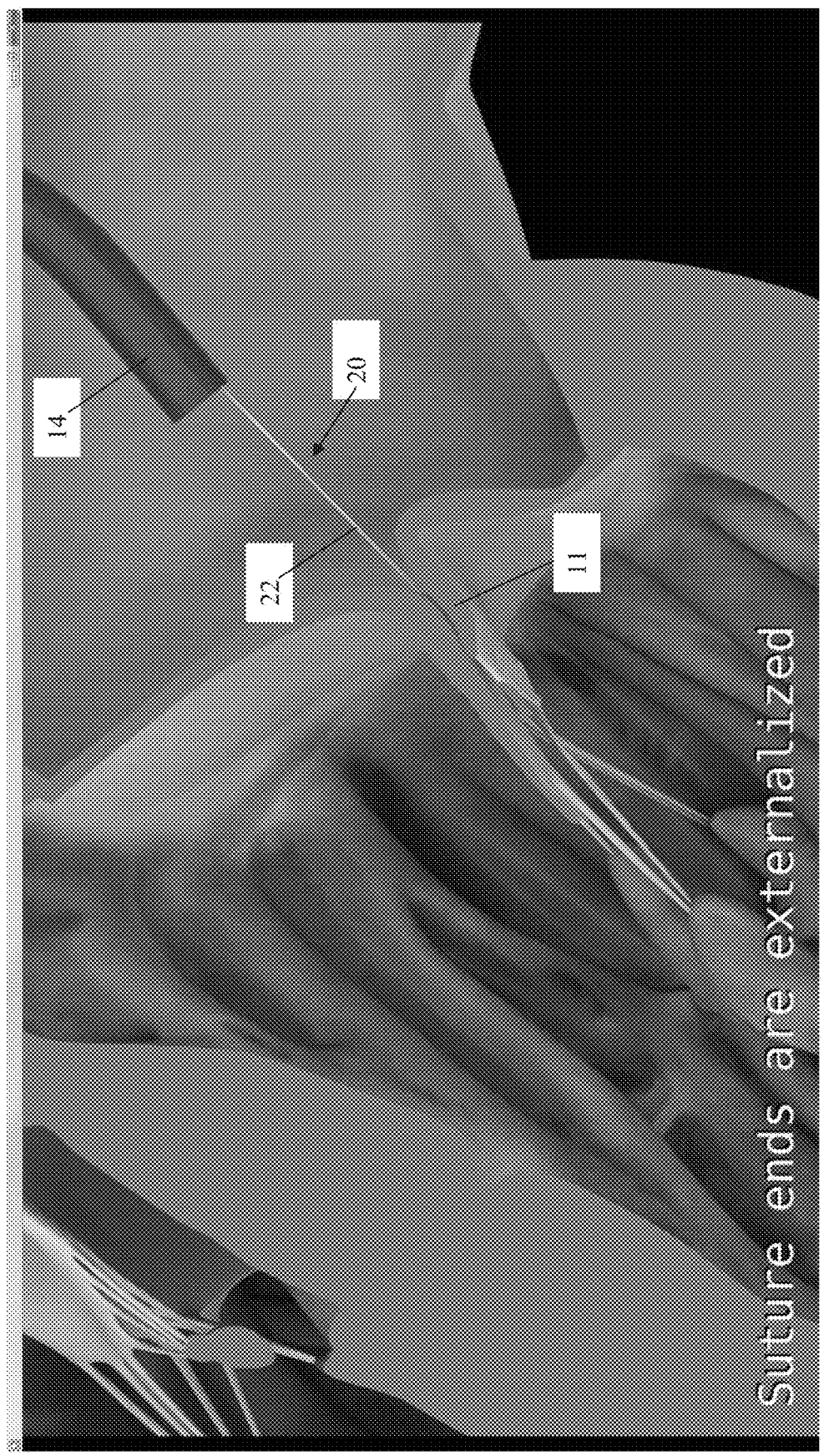

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The present disclosure is generally directed to anchoring of sutures inserted as artificial chordae into one or more heart valve leaflets through an intravascular, transcatheter approach. A heart valve leaflet may be captured and a suture inserted through the leaflet in any manner known in the art. One such leaflet capture catheter and procedure is disclosed in copending U.S. Utility patent application Ser. No. 16/363,701, which is hereby incorporated by reference herein. Another transcatheter procedure for inserting an artificial chordae is disclosed in U.S. Patent Publication No. 2016/0143737, which is hereby incorporated by reference herein.

Referring to FIGS. 1A-1K, a procedure for anchoring a suture inserted as an artificial chordae in a transcatheter procedure on a beating heart of a patient following insertion of the suture into a leaflet is schematically depicted. In this embodiment, a loop of suture has been inserted through the leaflet and the two free ends of the suture then inserted through the loop to form a girth hitch knot around the edge of the leaflet. Further detail regarding attaching a suture to a leaflet in this manner can be found in U.S. Patent Publication No. 2017/0290582, which is hereby incorporated by reference herein.

Figure 1B:
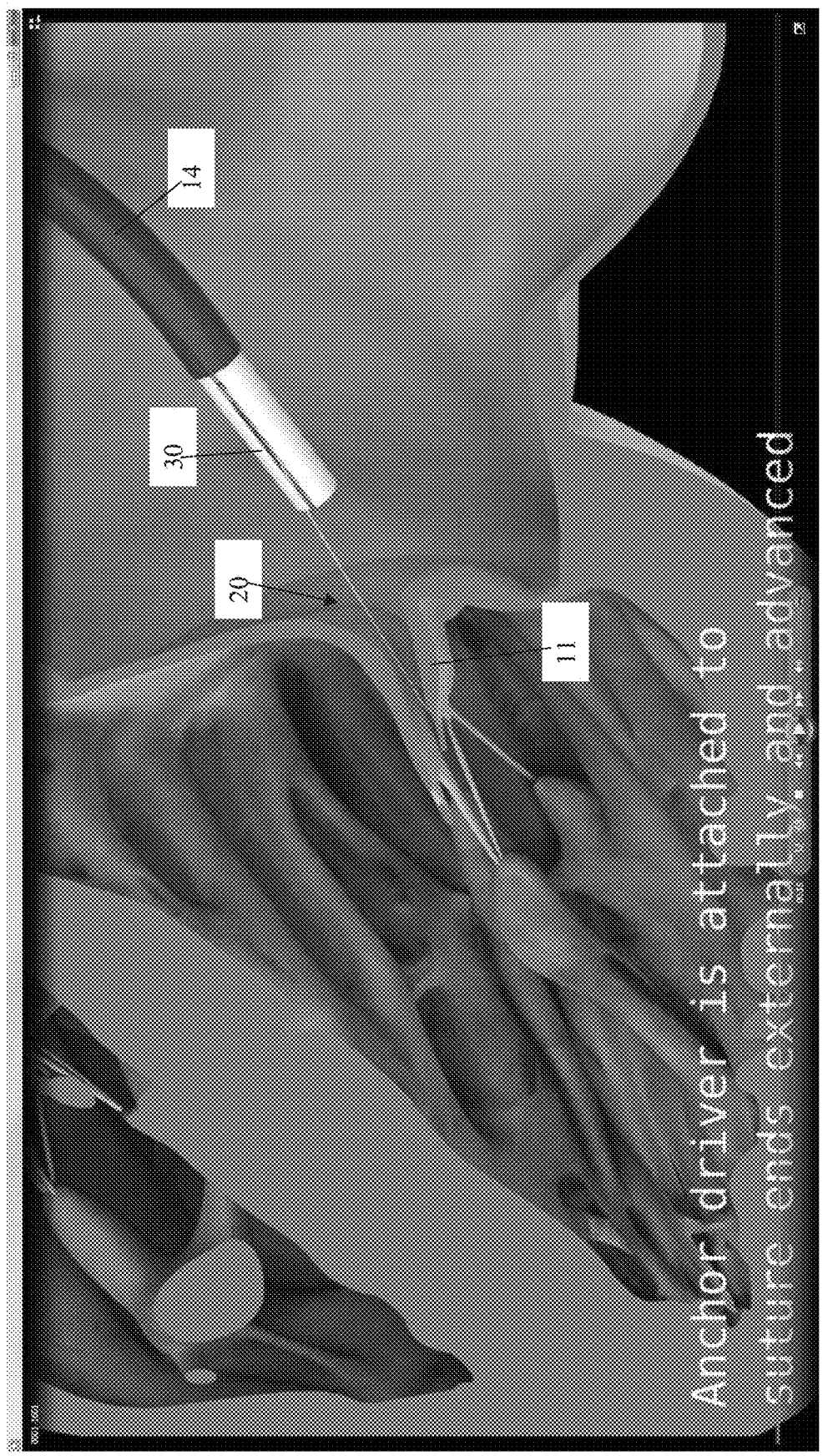
Figure 1D:
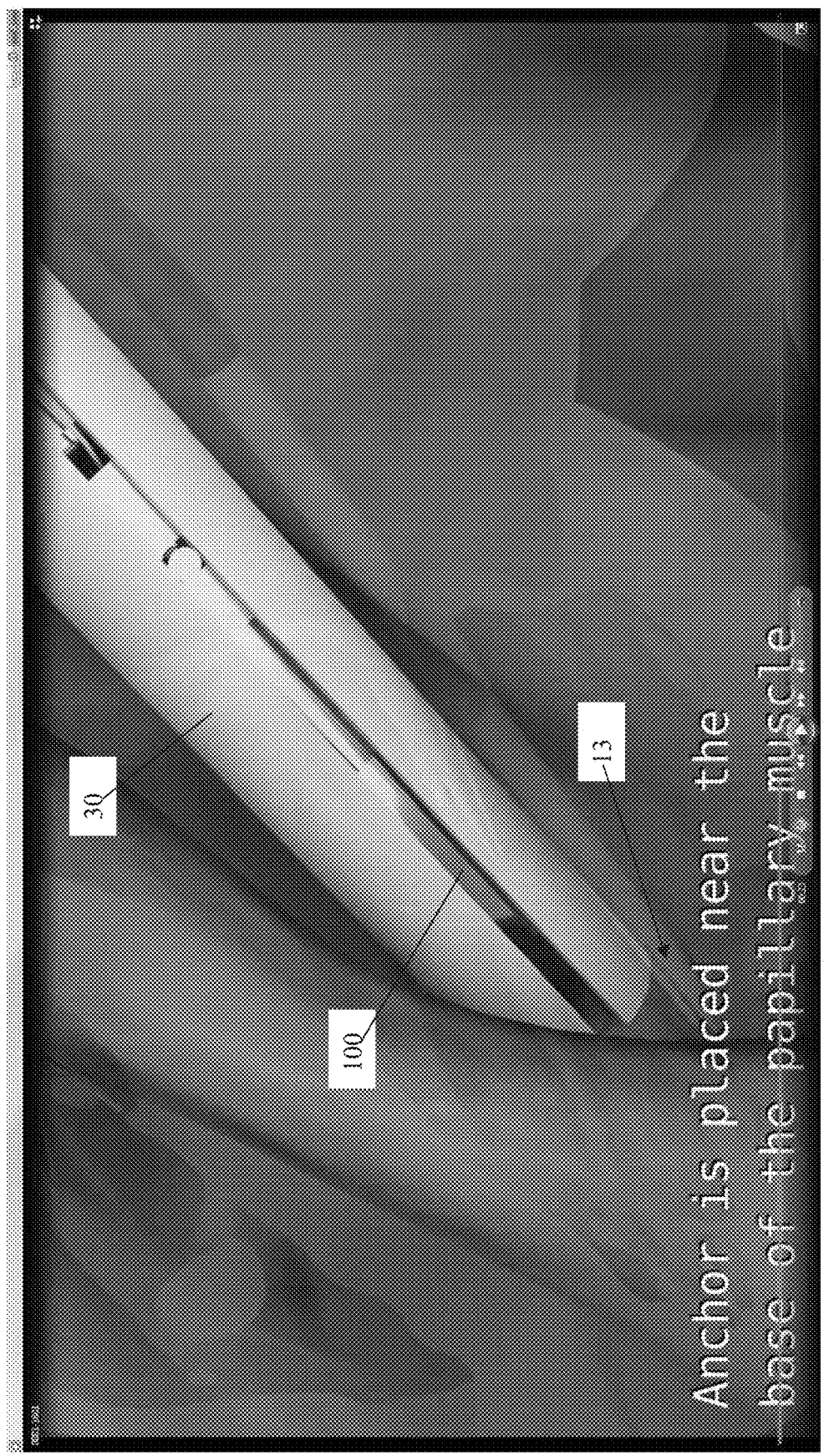
Figure 1E:
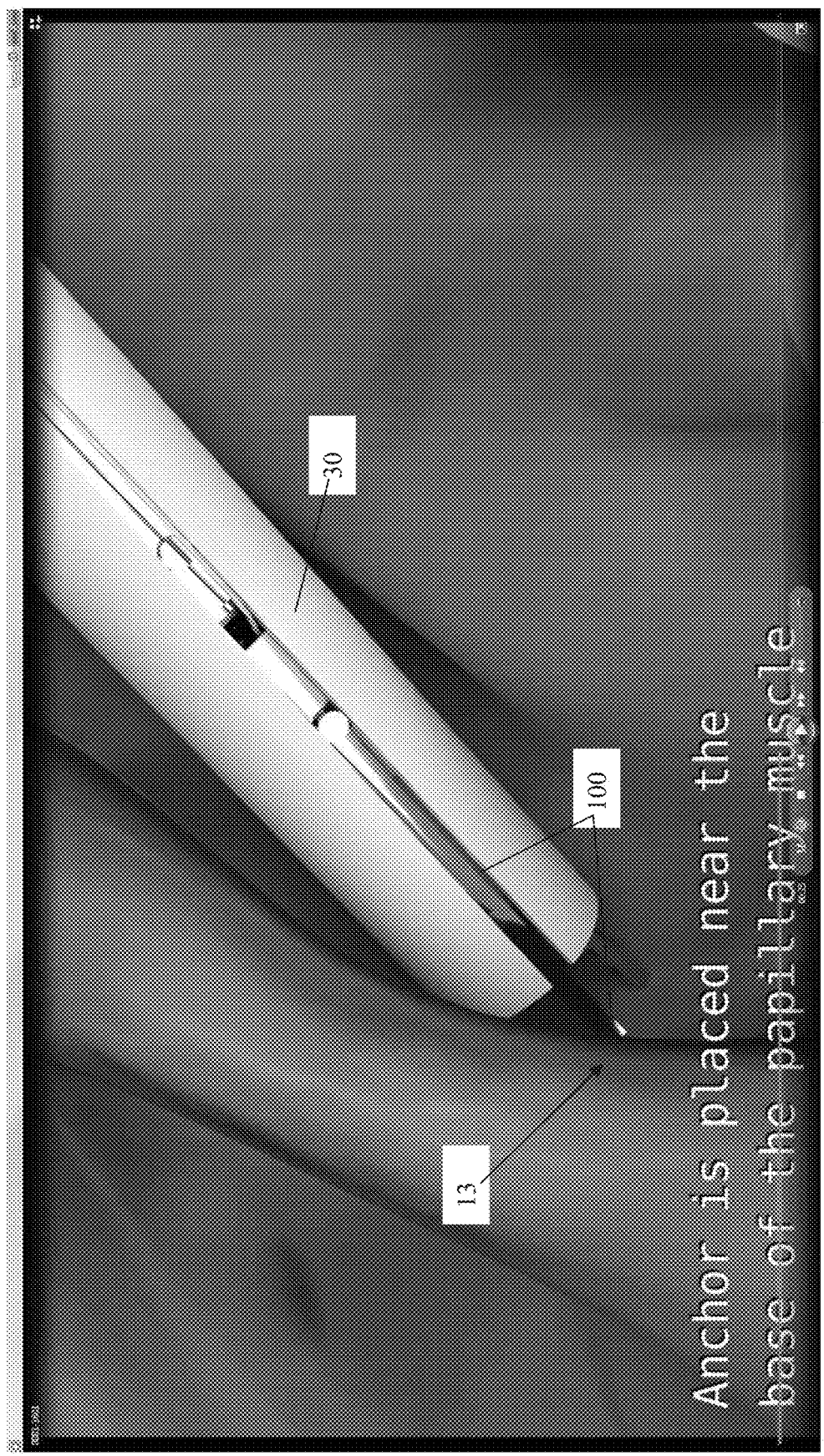
Figure 1F:
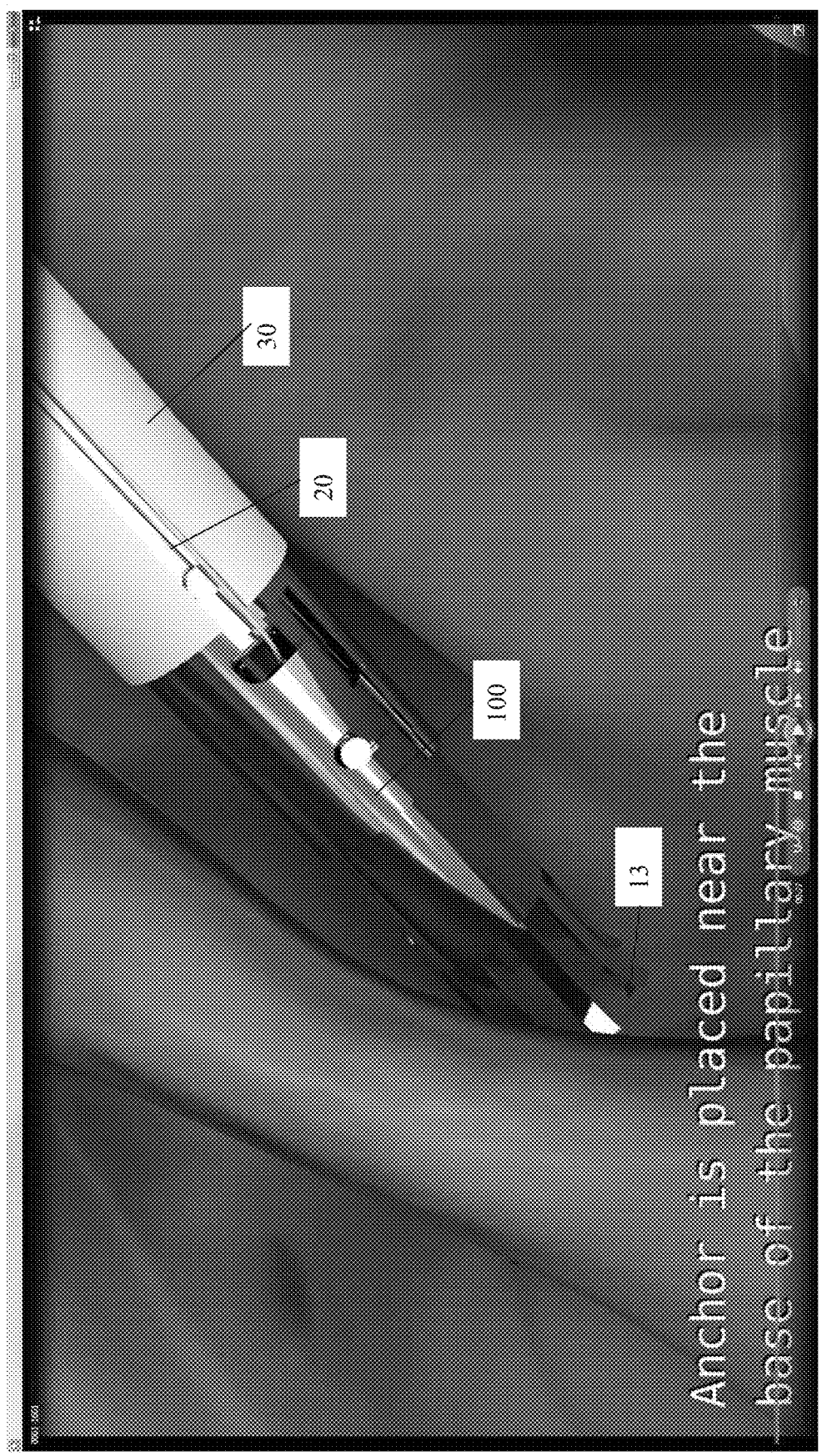
Figure 1G:
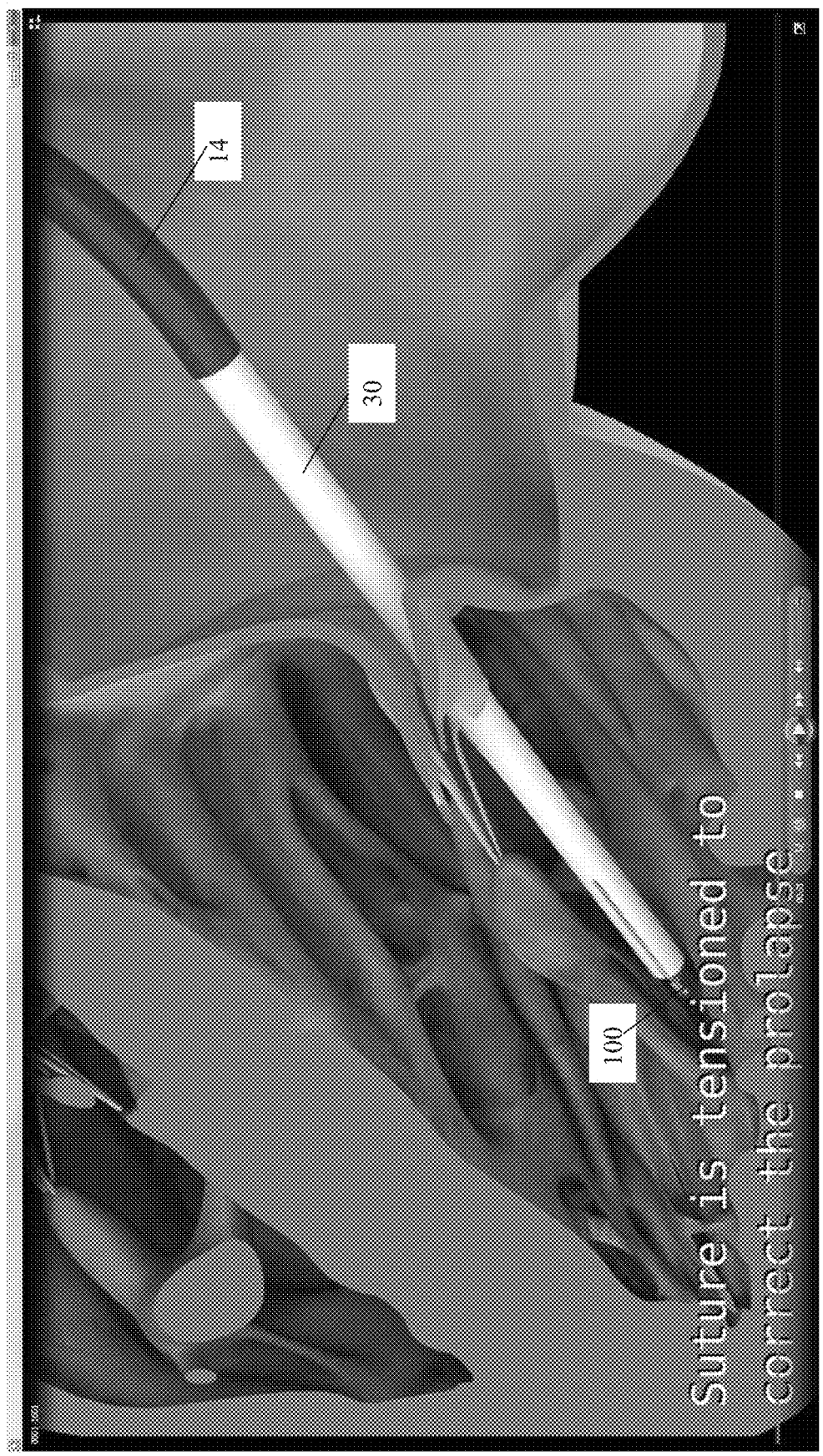

Following insertion of the suture 20 into the leaflet 11, the deployment catheter used to insert the suture is withdrawn through the guide catheter 14 and the two free ends 22 of the suture 20 are also withdrawn external to the body. The suture ends 22 are then attached to an anchor contained in an anchor driving catheter 30. Alternatively, the anchor could be pre-attached to the suture prior to insertion of the suture into the leaflet. The anchor driving catheter 30 is inserted into the guide catheter 14, routed through the catheter into the body and advanced passed the leaflet 11 to the heart wall 13 below the valve at, for example, a papillary muscle as shown in FIGS. 1B-1D. The anchor driving catheter 30 is then used to insert the anchor 100 into the myocardium as shown in FIGS. 1D-1G and as described in more detail below.

Figure 1H:
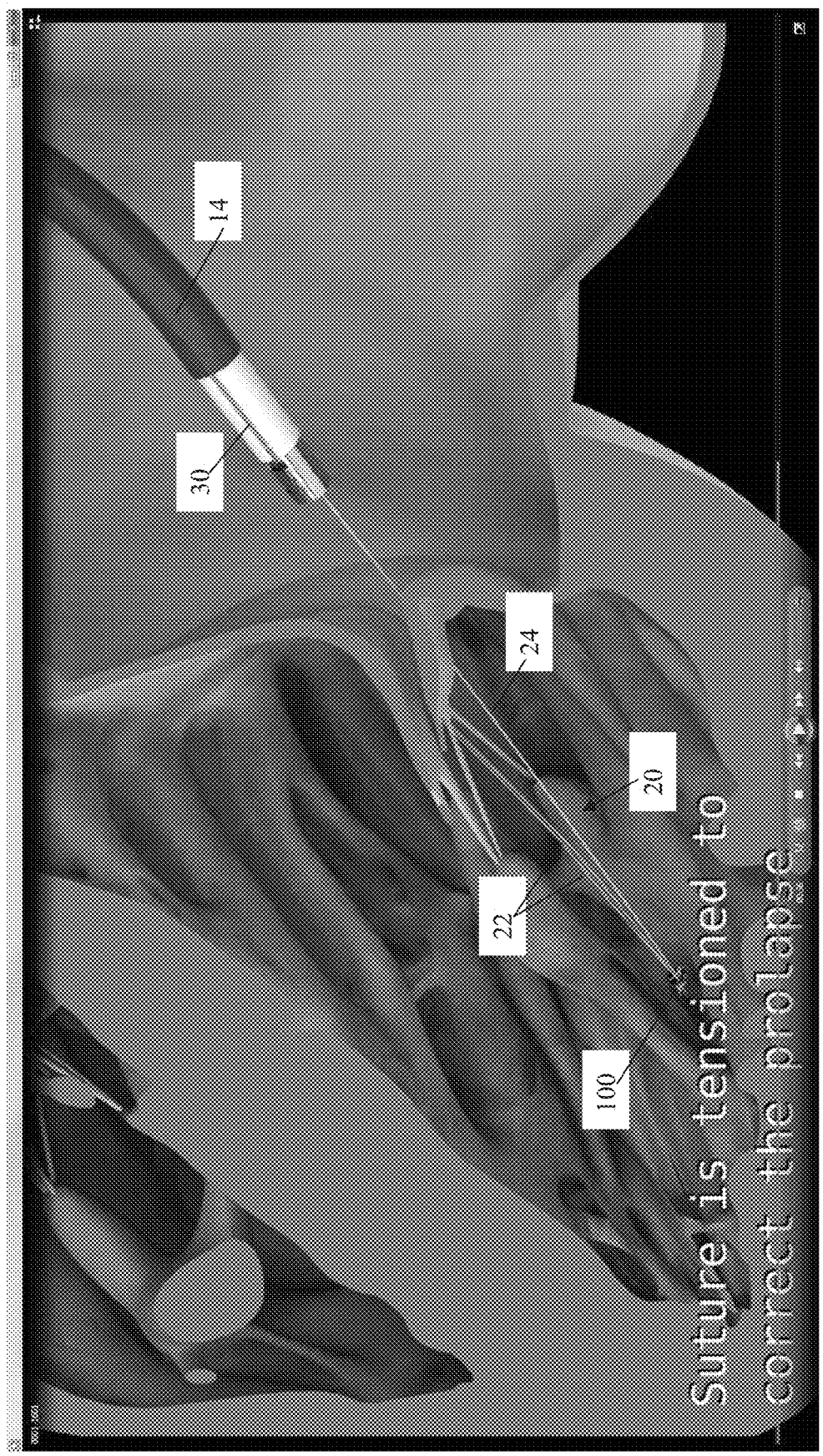
Figure 11:
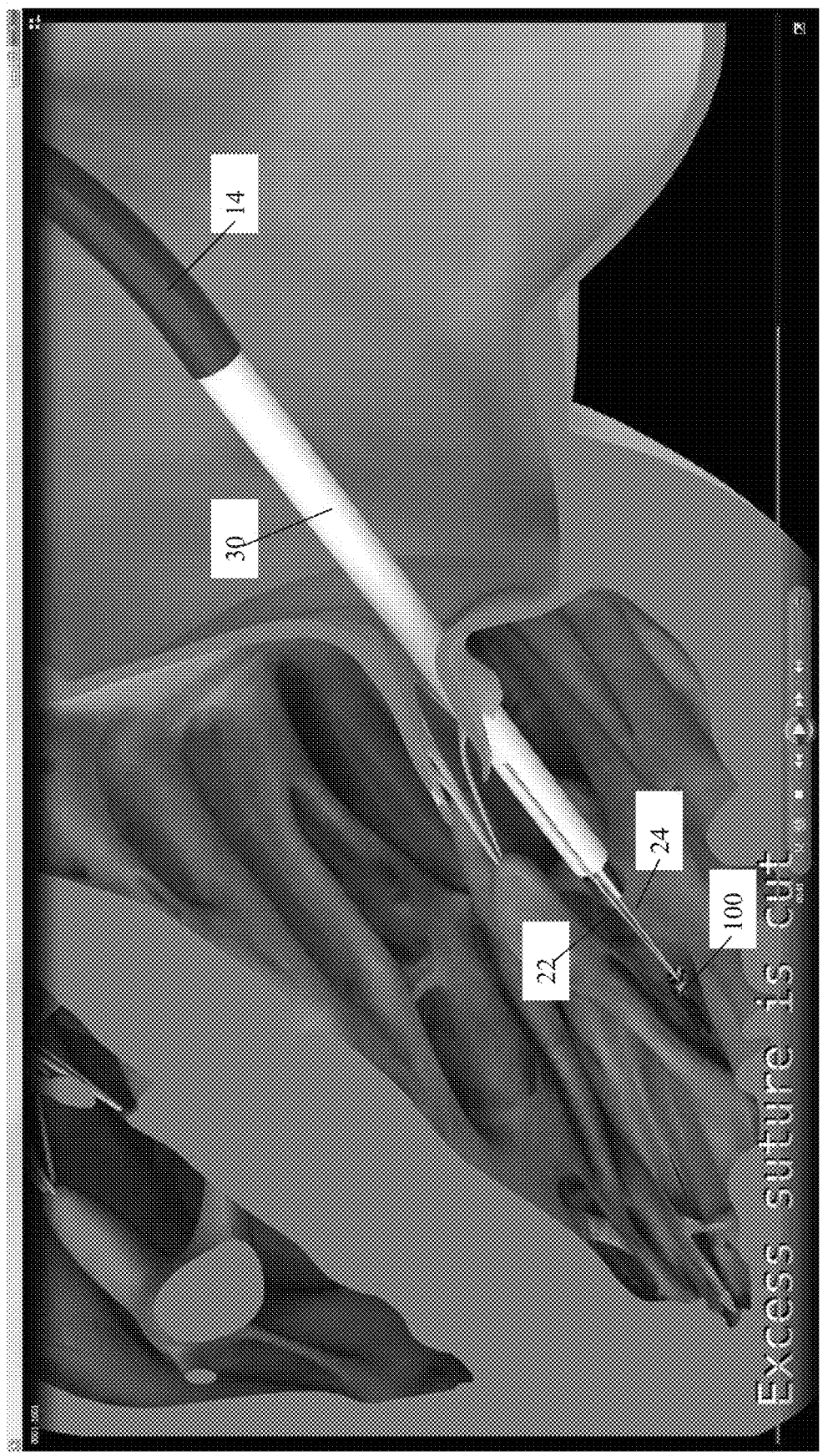
Figure 1J:
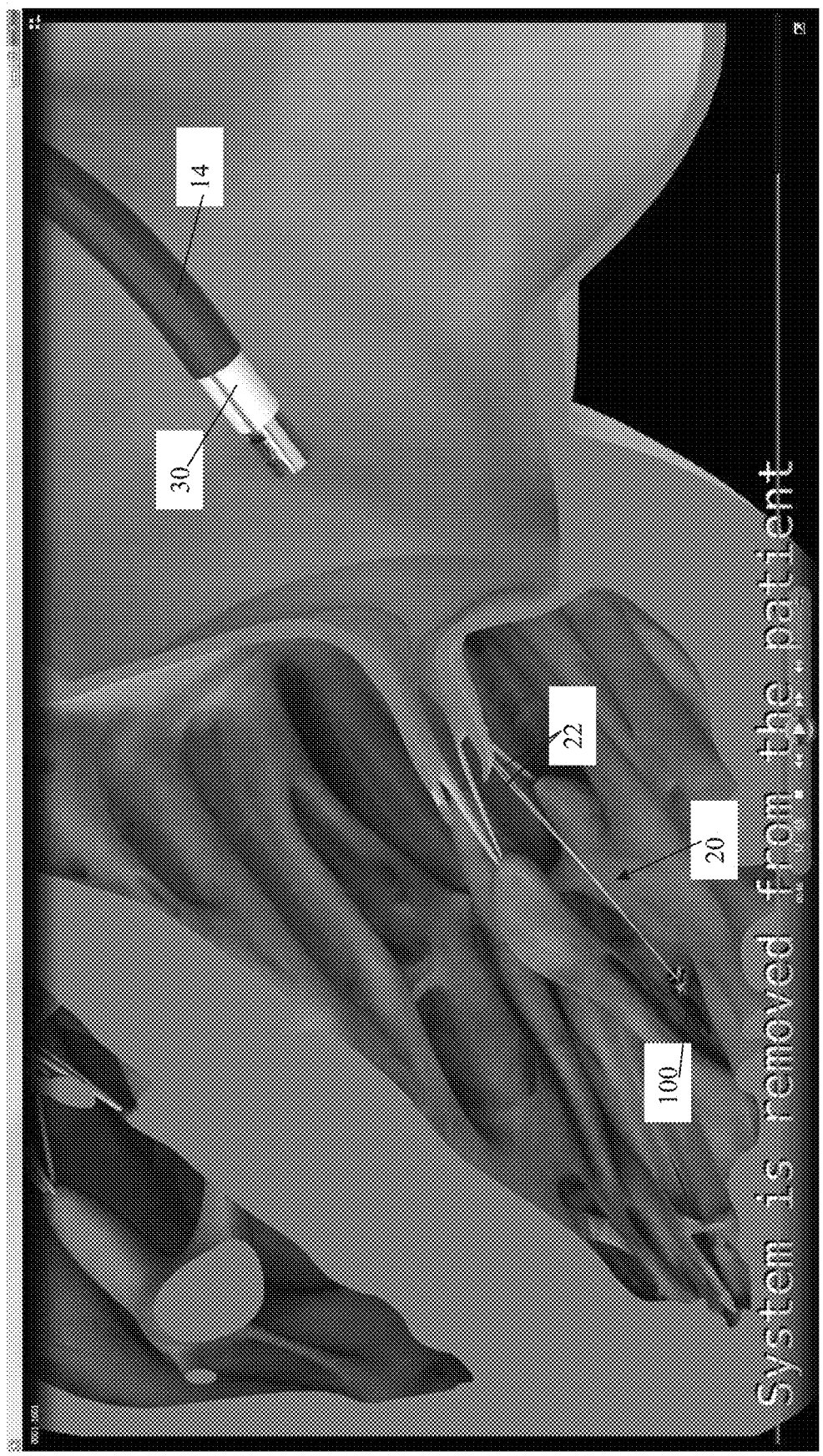

After insertion of the anchor 100 into the heart tissue, the anchor driving catheter 30 is withdrawn to a position superior of the valve as shown in FIG. 1H and the length and tension of the suture ends 22 extending from the leaflet 11 are tested and adjusted until it is determined that normal valve function has been achieved. This determination can be made through use of ultrasonic imaging, for example. The tension is adjusted through a tensioning strand 24 of the suture depicted in FIG. 1H. Once the proper length and tension has been determined using, for example, transesophageal echocardiography or other non-invasive methods, the anchor driving catheter 30 is advanced back down along the tensioning strand 24 and to sever the strand at the anchor 100. The entire catheter system, including the anchor driving catheter 30 and the guide catheter 14 is then withdrawn from the patient's body. Referring to FIG. 1K, the suture 20 remains in the body extending between the leaflet 11 and the anchor 100 to function as an artificial chordae tendineae Disclosed herein are various embodiments of anchors that can be employed in procedures such those described above to anchor a suture as an artificial chordae. Such anchors maintain positioning and length of the suture (i.e., tension) to ensure proper leaflet functionality during the cardiac cycle.

Figure 2:
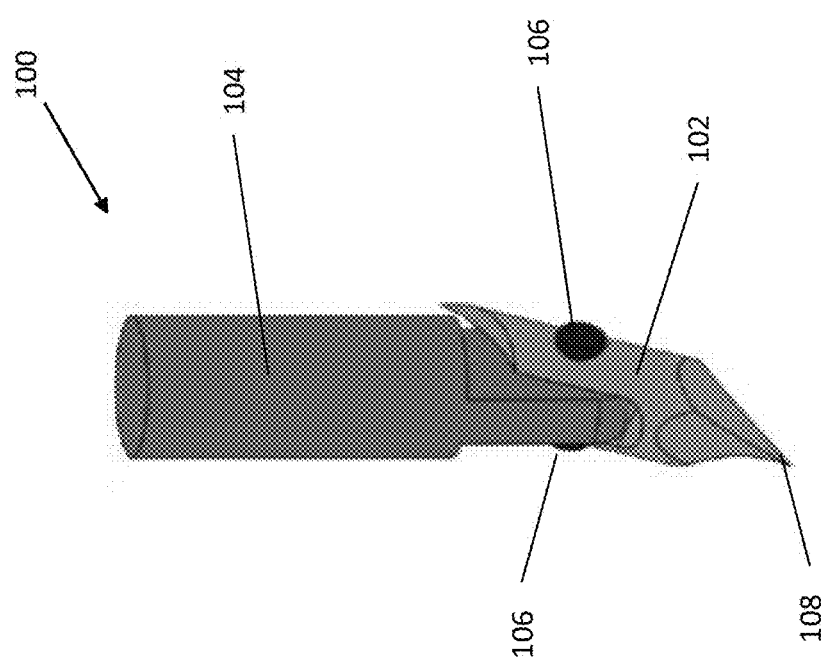
FIG. 2 depicts a low profile tissue anchor for an artificial chordae according to an embodiment.

Referring now to FIG. 2, one embodiment of a low profile tissue anchor or "toggle anchor" 100 for anchoring a suture as an artificial chordae is depicted. Toggle anchor 100 generally includes an anchor tip 102 and an anchor shaft 104. Anchor tip 102 can be configured to pivot with respect to anchor shaft 104. In one embodiment, anchor tip 102 can be connected to anchor shaft 104 with a pin 106. Pin 106 can be configured as a generally cylindrical rod extending through aligned apertures in the anchor shaft 104 and the anchor tip 102 to enable the anchor tip to pivot about pin 106 with respect to anchor shaft.

Figure 3C:
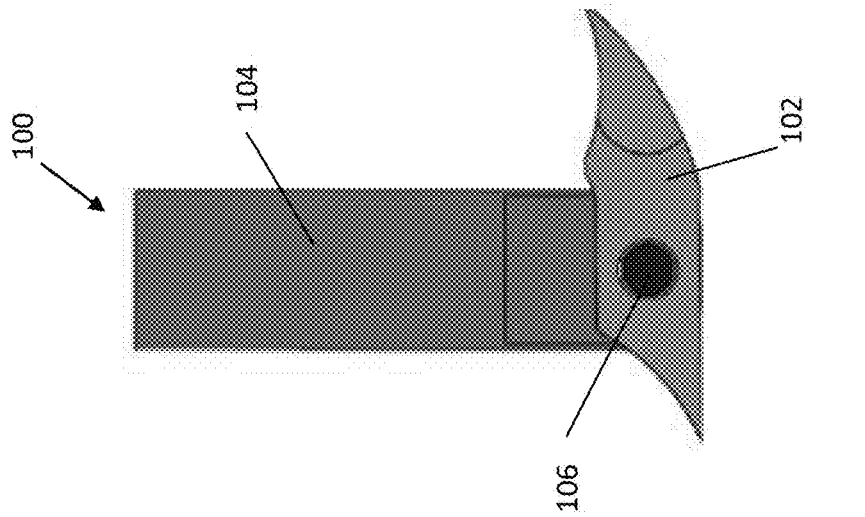
FIGS. 3A-3C depict a low profile tissue anchor for an artificial chordae according to an embodiment.
Figure 3B:
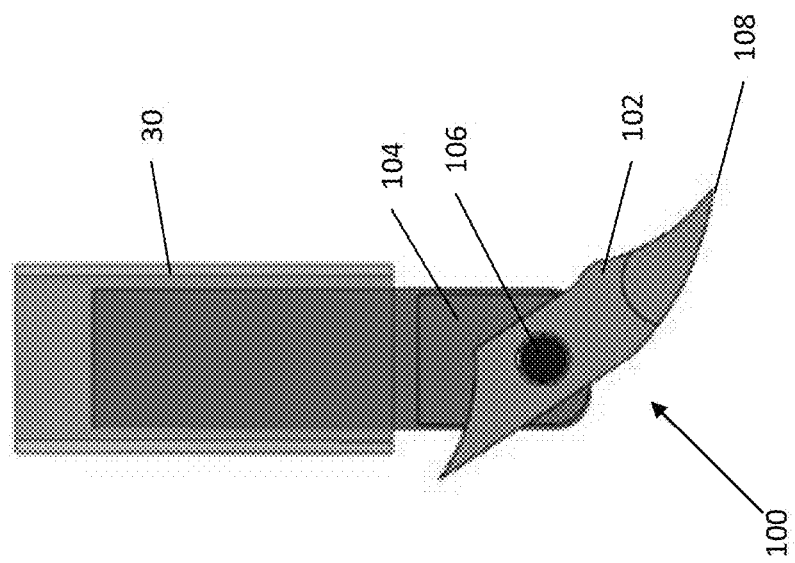
Figure 3A:
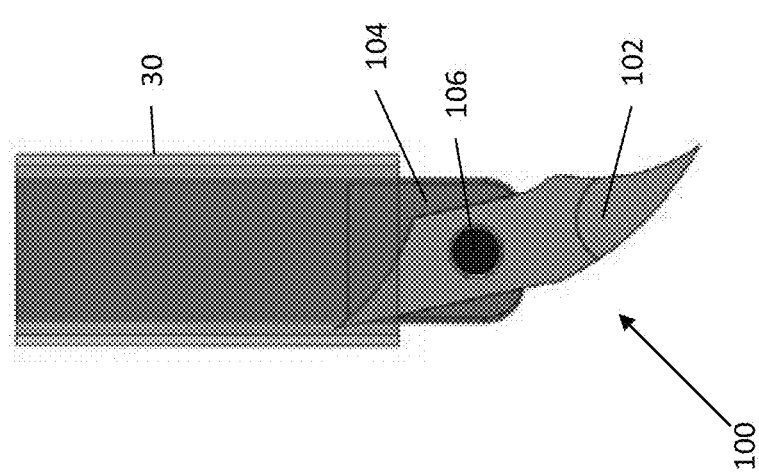

FIGS. 3A-3C depict various configurations that one embodiment of a low profile tissue anchor or toggle anchor 100 as depicted in FIG. 2 can take on to enable the toggle anchor to be delivered through the guide catheter into the heart and anchored within the myocardium of the heart. FIG. 3A depicts a delivery position or configuration of the toggle anchor 100 for when the anchor 100 and anchor driving catheter 30 are guided through the guide catheter 14 and the anchor driving catheter 30 is advanced adjacent the myocardium. In this configuration, the anchor tip 102 is generally longitudinally aligned with the anchor shaft 30, which enables the anchor 100 to be contained within the anchor driving catheter 30 so that the anchor 100 can be routed through the guide catheter 14.

Adjacent the myocardium, the anchor tip 102 is advanced out of the anchor driving catheter 30 and as the anchor edge 108 is driven into the myocardium, the anchor tip 102 pivots with respect to the anchor shaft 104 about pin 106 as shown in FIG. 3B. In one embodiment, the anchor tip 102 automatically pivots when advanced out of the anchor driving catheter 30 when it is no longer constrained into the delivery position by the anchor driver 30, which provides the necessary force to insert the anchor tip 102 into the heart wall. In another embodiment, the anchor tip 102 pivots due to a force of the beating heart wall on the anchor tip 102. As the anchor tip 102 is further driven into the heart muscle, the anchor tip 102 can continue to rotate to a final, anchoring position transverse to the anchor shaft 106 that inhibits inadvertent removal of the anchor tip 102. In the depicted embodiment, the anchor tip 102 is oriented at a generally 90 degree angle with respect to the anchor shaft 106 in the anchoring position. In various embodiments, the anchor tip 102 can be oriented at other angles, such as a 45 degree angle, 60 degree angle, or any angle between about 45 degrees and about 90 degrees. The anchor tip 102 and, in some embodiments, the anchor shaft 104 then remain in the body with one or more sutures extending between the anchor 100 and a leaflet as an artificial chordae. In one embodiment, anchor shaft 104 includes a tensioning mechanism through which a tension on the suture can be adjusted. Examples of such tensioning mechanisms can be found in U.S. Provisional Patent Application No. 62/669,115 filed May 9, 2018, entitled Suture Length Adjustment for Minimally Invasive Heart Valve Repair, which is hereby incorporated by reference herein in its entirety.

FIGS. 4A-4C depict a low profile tissue anchor or toggle anchor 200 according to another embodiment. Toggle anchor 200 can include an anchor tip 202 and an anchor shaft 204. The suture 20 can extend through a suture lumen 206 in the anchor shaft 202, into a tip lumen 208 in the anchor tip 206 and attach to the anchor tip 202 at a suture attachment point 210 within tip lumen 208. As shown in FIG. 4B, anchor shaft 204 can be selectively detachable from anchor tip 202. In practice, tension in the suture 20 holds the anchor tip 202 proximally against the anchor shaft 204 with a distal shaft connector 214 seated within the tip lumen 208 of the anchor tip 202 as the anchor 200 is advanced to the myocardium with the anchor driver 30 (not pictured in FIGS. 4A-4C). The anchor driver 30 drives the anchor edge 212 into the myocardium to insert the anchor tip 202 into the heart muscle. As the anchor tip 102 is driven into the heart wall, the anchor can automatically pivot from the generally longitudinally position shown in FIGS. 4A-4B to the more transverse position shown in FIG. 4C to inhibit accidental removal of the anchor from the tissue. As the anchor tip 202 is inserted into the heart wall, the anchor shaft 204 disengages from the anchor tip 202 and can then be withdrawn from the body along the suture 20. The anchor tip 202 remains embedded in the heart wall with the suture 20 extending therefrom to a valve leaflet.

FIGS. 5A-5D depict a low profile tissue anchor or toggle anchor 300 according to a further embodiment. Toggle anchor 300 includes an anchor body 302 having one or more anchor tips extending distally therefrom. A suture (not pictured) can be attached to toggle anchor 300 within anchor body 300. In one embodiment, anchor tips can be configured as tines 304 that are unitarily formed with anchor body 302 in a monolithic construction. Four tines 304 extend radially around anchor body 302 in the depicted embodiment, but toggle anchors having greater or fewer tines can be utilized, including embodiments having only a single tine. Tines 304 function similarly to anchor tips 102 above that pivot to anchor within the tissue such that the tines function as a hingeless toggle.

Figure 5B:
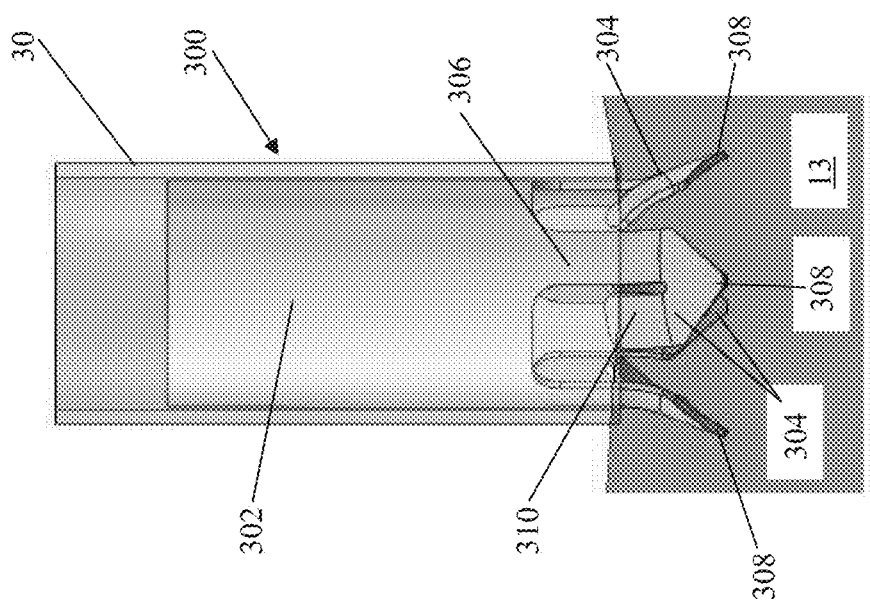
FIGS. 5A-5D depict a low profile tissue anchor for an artificial chordae according to an embodiment.
Figure 5A:
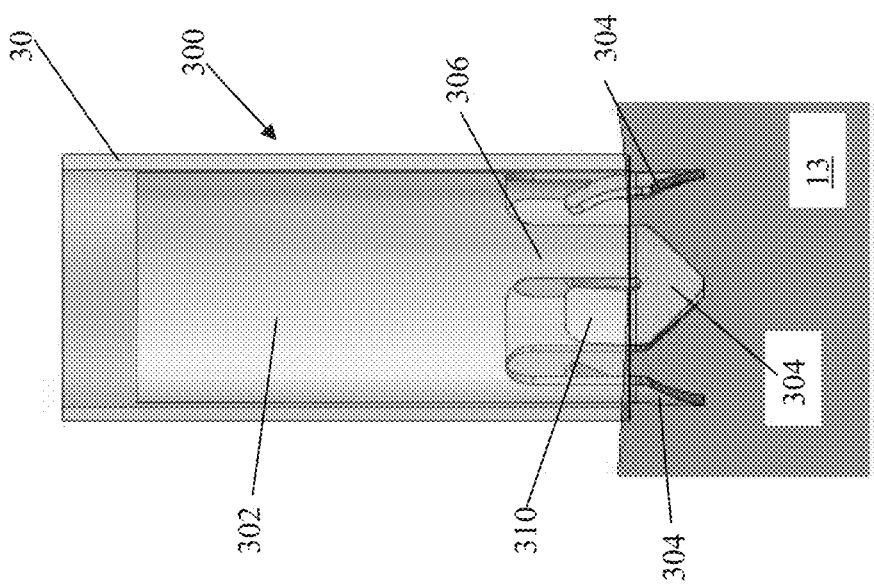
Figure 5D:
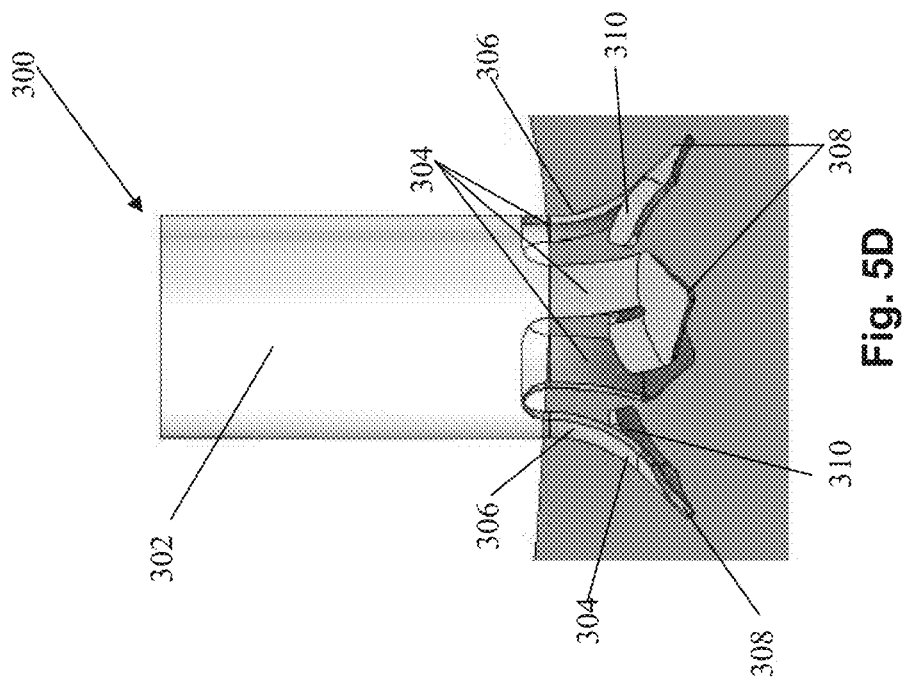
Figure 5C:
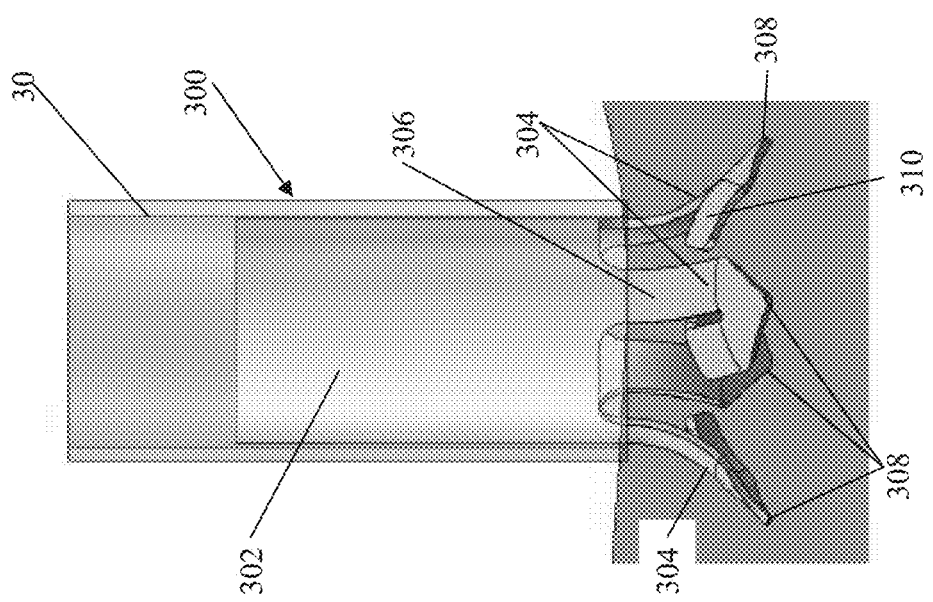

Still referring to FIGS. 5A-5D, each tine 304 can include an arm 306 that unitarily extends from a distal end of the anchor body 302 of toggle anchor 300. Tines 304 each further include a pointed tip 308 and a leg 310 extending from the tip 308 proximally back towards the anchor body 302. Tines 304 can each be biased outwardly towards an anchoring configuration. In one embodiment, this is accomplished by forming tines 304 or toggle anchor 300 from a shape memory material such as, for example, Nitinol. As depicted in FIG. 5A, tines 304 can take on a longitudinal delivery configuration in which the tines 304 extend generally axially with respect to the anchor body 302 when constrained by the anchor driving catheter 30. As the toggle anchor 300 is advanced distally from the anchor driver 30 and into the heart muscle 13, the tines 304 automatically toggle into the anchoring configuration as shown in FIGS. 5B and 5C. This toggling motion creates the necessary force to drive the tines 304 into the heart muscle 13. In the depicted embodiment, the tines 304 are oriented at a generally 45 degree angle with respect to the anchor body 302. In various embodiments, the tines 304 can be oriented at various other angles, such as, for example, 60 degrees, 90 degrees or any angle between about 45 degrees and about 90 degrees. Once the tines 304 are generally fully inserted into the heart wall 13, the anchor driving catheter 30 can be withdrawn with the toggle anchor 100 firmly retained in the heart. In one embodiment, the legs 310 of tines 304 are offset from the tine arms 306 to increase the pullout force required for the anchor to be removed to more stably seat the anchor in the heart wall 13, as can be seen in, for example, FIG. 5D. In some embodiments, anchor body 302 can include a tensioning mechanism for adjusting a tension on the suture, as described above.

Disclosed herein are various embodiments of anchors configured to be inserted into a heart wall of a patient to anchor a suture as an artificial chordae under an appropriate tension for proper valve function. Each of the disclosed anchor embodiments "toggles" from a first position for delivery of the anchor to the heart wall and a second position for insertion of the anchor into the heart wall. In some embodiments, it is this "toggle" that provides the insertion force for inserting the anchor into the heart muscle sufficient to retain the anchor from accidental withdrawal from the heart wall during normal valve operation (e.g., when a valve leaflet pulls on the suture attached to the anchor during systole). Such anchors are particularly suitable for use in intravascular, transcatheter procedures as described above given the inherent difficulties in providing sufficient force for insertion of an anchor into the heart wall with a flexible catheter.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

The invention claimed is:

1. A method of anchoring a suture in a heart of a patient as an artificial chordae, comprising:
   intravascularly accessing the heart;
   inserting a suture into a heart valve leaflet of the heart;
   attaching a portion of the suture to a tissue anchor, the tissue anchor including an anchor body and only a single anchor tip;
   advancing the tissue anchor into the heart with an anchor delivery catheter with the tissue anchor in a delivery position having the single anchor tip extending generally coaxially with respect to the anchor body such that the tissue anchor fits within the anchor delivery catheter;
   positioning the tissue anchor adjacent a heart wall of the heart;
   advancing the tissue anchor out of the anchor delivery catheter and into the heart wall such that the tissue anchor transitions from the delivery position into an anchoring position as the tissue anchor is advanced into the heart wall, the single anchor tip being oriented at a non-coaxial angle to the anchor body in the anchoring position, and wherein the transition from the delivery position and anchoring position provides a force sufficient to cause the single anchor tip to penetrate into the heart wall; and
   removing the anchor delivery catheter from the heart leaving the tissue anchor in the heart with the suture extending between the leaflet and the tissue anchor as an artificial chordae.

2. The method of claim 1, wherein the tissue anchor transitions from the delivery position into an anchoring position automatically when the single anchor tip is advanced out of the anchor delivery catheter.

3. The method of claim 1, wherein the tissue anchor transitions from the delivery position into the anchoring position as the tissue anchor is advanced into the heart wall by the single anchor tip contacting the heart wall.

4. The method of claim 1, wherein the tissue anchor transitions from the delivery position into the anchoring position by the single anchor tip pivoting with respect to the anchor body.

5. The method of claim 4, wherein the single anchor tip pivots with respect to the anchor body about a pin.

6. The method of claim 1, further comprising disconnecting the anchor body from the single anchor tip and removing the anchor body from the heart.

7. The method of claim 1, further comprising adjusting a tension of the suture.

8. The method of claim 1, wherein the single anchor tip being oriented at a non-coaxial angle to the anchor body in the anchoring position orients the single anchor tip at an angle of greater than 45 degrees relative to the anchor body.

9. The method of claim 1, wherein the single anchor tip being oriented at a non-coaxial angle to the anchor body in the anchoring position orients the single anchor tip at an angle of about 90 degrees relative to the anchor body.

10. A method of anchoring a suture in a heart of a patient as an artificial chordae, comprising:
    intravascularly accessing the heart;
    inserting a suture into a heart valve leaflet of the heart;
    attaching a portion of the suture to a tissue anchor, the tissue anchor include an anchor body and an anchor tip such that the suture extends through the anchor body to the anchor tip and tension in the suture holds the anchor tip proximally against the anchor shaft prior to implantation;
    advancing the tissue anchor into the heart with an anchor delivery catheter with the tissue anchor in a delivery position having the anchor tip extending generally coaxially with respect to the anchor body such that the tissue anchor fits within the anchor delivery catheter;
    positioning the tissue anchor adjacent a heart wall of the heart;
    advancing the tissue anchor out of the anchor delivery catheter and into the heart wall such that the tissue anchor transitions from the delivery position into an anchoring position as the tissue anchor is advanced into the heart wall, the anchor tip being oriented at a non-coaxial angle to the anchor body in the anchoring position, and wherein the transition from the delivery position to the anchoring position provides a force sufficient to cause the anchor tip to penetrate into the heart wall and causes the anchor tip to disengage from the anchor body;
    sliding the anchor body back along the suture away from the anchor tip; and
    removing the anchor delivery catheter and the anchor body from the heart leaving the anchor tip in the heart with the suture extending between the leaflet and the anchor tip as an artificial chordae.

11. The method of claim 10, wherein the tissue anchor transitions from the delivery position into an anchoring position automatically when the anchor tip is advanced out of the anchor delivery catheter.

12. The method of claim 10, wherein the tissue anchor transitions from the delivery position into the anchoring position as the tissue anchor is advanced into the heart wall by the anchor tip contacting the heart wall.

13. The method of claim 10, wherein the tissue anchor transitions from the delivery position into the anchoring position by the anchor tip pivoting with respect to the anchor body.

14. The method of claim 10, further comprising adjusting a tension of the suture.

15. The method of claim 10, wherein the anchor tip being oriented at a non-coaxial angle to the anchor body in the anchoring position orients the anchor tip at an angle of greater than 45 degrees relative to the anchor body.

16. The method of claim 10, wherein the anchor tip being oriented at a non-coaxial angle to the anchor body in the anchoring position orients the anchor tip at an angle of about 90 degrees relative to the anchor body.

* * * * *